United States Patent
Carrier

(10) Patent No.: US 9,642,638 B1
(45) Date of Patent: May 9, 2017

(54) MORCELLATED TISSUE COLLECTION POUCH

(71) Applicant: Vicki J. Carrier, Lantana, FL (US)

(72) Inventor: Vicki J. Carrier, Lantana, FL (US)

( * ) Notice: Subject to any disclaimer, the term of this patent is extended or adjusted under 35 U.S.C. 154(b) by 164 days.

(21) Appl. No.: 14/584,306

(22) Filed: Dec. 29, 2014

Related U.S. Application Data

(60) Provisional application No. 61/974,085, filed on Apr. 2, 2014.

(51) Int. Cl.
*A61B 17/24* (2006.01)
*A61B 17/26* (2006.01)
*A61B 17/221* (2006.01)

(52) U.S. Cl.
CPC .... *A61B 17/221* (2013.01); *A61B 2017/2212* (2013.01)

(58) Field of Classification Search
CPC .... A61B 2017/00287; A61B 17/00234; A61B 17/221; A61B 2017/320064; A61B 2017/320024; A61B 2017/2212; A61B 2017/4216
USPC .......................... 606/110, 113, 114; 383/204
See application file for complete search history.

(56) References Cited

U.S. PATENT DOCUMENTS

| | | | |
|---|---|---|---|
| 4,452,245 A | 6/1984 | Usher | |
| 4,950,258 A | 8/1990 | Kawai et al. | |
| 4,991,978 A * | 2/1991 | Ostrowski | A45C 3/10 383/13 |
| 5,037,379 A | 8/1991 | Clayman et al. | |
| 5,074,867 A | 12/1991 | Wilk | |
| 5,092,681 A * | 3/1992 | Ashley, III | B65D 33/28 383/4 |
| 5,405,360 A * | 4/1995 | Tovey | A61B 17/00234 606/151 |
| 6,409,733 B1 * | 6/2002 | Conlon | A61B 17/00234 600/37 |
| 6,669,706 B2 | 12/2003 | Schmitt et al. | |
| 7,582,576 B2 | 9/2009 | Snijder et al. | |
| 2004/0210027 A1 | 10/2004 | Hayashi et al. | |
| 2005/0063622 A1* | 3/2005 | Kannabiran | B65D 33/28 383/75 |
| 2005/0119688 A1* | 6/2005 | Bergheim | A61F 2/013 606/200 |
| 2006/0195118 A1* | 8/2006 | Richardson | A61B 17/221 606/113 |
| 2006/0200169 A1 | 9/2006 | Sniffin | |
| 2006/0200170 A1* | 9/2006 | Aranyi | A61B 17/00234 606/113 |
| 2007/0016251 A1* | 1/2007 | Roby | A61L 17/04 606/228 |
| 2007/0135781 A1* | 6/2007 | Hart | A61B 17/00234 604/327 |

(Continued)

FOREIGN PATENT DOCUMENTS

| EP | 0930047 A1 | 7/1999 |
|---|---|---|
| EP | 1700569 A1 | 1/2006 |
| EP | 2353545 A1 | 1/2011 |

*Primary Examiner* — Katherine M Shi
(74) *Attorney, Agent, or Firm* — Robert C. Montgomery; Montgomery Patent & Design LP.

(57) ABSTRACT

An apparatus for collection and removal of morcellated tissue includes a flexible sheet material including a top surface and a bottom surface. The sheet material is configurable from a roll configuration, to a substantially planar mat configuration, to a pouch configuration.

14 Claims, 5 Drawing Sheets

(56) References Cited

U.S. PATENT DOCUMENTS

| | | | |
|---|---|---|---|
| 2011/0184431 A1* | 7/2011 | Parihar | A61B 17/00 |
| | | | 606/114 |
| 2011/0184432 A1* | 7/2011 | Parihar | A61B 17/00234 |
| | | | 606/114 |
| 2012/0277758 A1 | 11/2012 | Davis et al. | |
| 2013/0068169 A1* | 3/2013 | Miller | A01K 1/0107 |
| | | | 119/161 |
| 2014/0252052 A1* | 9/2014 | Shlafer | A47G 9/062 |
| | | | 224/153 |

* cited by examiner

MORCELLATED TISSUE COLLECTION POUCH

RELATED APPLICATIONS

The present invention was first described in and claims the benefit of U.S. Provisional Application No. 61/974,085, filed Apr. 2, 2014, the entire disclosures of which are incorporated herein by reference.

FIELD OF THE INVENTION

The present invention relates generally to tissue collection and, more particularly, to a morcellated tissue collection pouch having a propensity to maintain a flat shape and a means to form a pocket to capture and contain the morcellated tissue.

BACKGROUND OF THE INVENTION

There are many different types of surgery in which a fibroids or tumor-like objects need to be removed from an internal body cavity. In many of these cases, the tissue to be removed is larger than the opening made in the body. In this instance, the tissue must be "morcellated" or broken up into smaller pieces that can be removed.

Unfortunately, this morcellation process can result in fragments or pieces that may be dispersed throughout the body cavity. This then takes the surgeon additional time to search for and remove these pieces. Additionally, this searching time often requires other organs to be disturbed resulting in additional pain for the patient and increased recovery time.

Accordingly, there exists a need for a means by which morcellated tissue can be easily captured, retained, and removed during surgery, in a manner which addresses the above problems.

SUMMARY OF THE INVENTION

The inventor has recognized the aforementioned inherent problems and lack in the art and observed that there is a need for a morcellated tissue collection apparatus that provides for enhanced collection of morcellated tissue during surgery, in a manner that is not only quick, easy, and effective, but results in increased quality of care for the patient as well. The development of the present invention, which will be described in greater detail herein, substantially departs from conventional solutions to fulfill this need.

In one embodiment, the disclosed apparatus for collection and removal of morcellated tissue includes a flexible sheet material including a top surface and a bottom surface. The sheet material is configurable from a roll configuration, to a substantially planar mat configuration, to a pouch configuration.

In another embodiment, the disclosed apparatus for collection and removal of morcellated tissue includes a flexible sheet material including a rectangular shape, the sheet material further including a top surface for collecting the mocellated tissue, a bottom surface opposite the top surface, and a perimeter edge. The apparatus further includes a cinch string operably coupled to the perimeter edge. The sheet material is configurable from a roll configuration for insertion into a human body, to a substantially planar mat configuration for collection of the morcellated tissue, to a pouch configuration for removal of the morcellated tissue from the human body.

In another embodiment, the disclosed method for collecting and removing morcellated tissue from a human body during a laparoscopic procedure includes the steps of: 1). providing a flexible sheet material in a roll configuration, the sheet material including a top surface, a bottom surface, and a perimeter edge, and a cinch string operably coupled to the perimeter edge of the flexible sheet material, 2). inserting said sheet material in the rolled configuration into the human body, 3). reconfiguring the sheet material into a substantially planar mat configuration, the sheet material including a barrier extending upwardly from the top surface along at least a portion of the perimeter edge, the barrier including a coiled wire capable of biasing the sheet material in the mat configuration, 4). collecting the morcellated tissue on the top surface, 5). retaining the morcellated tissue on the top surface by the barrier. 6). removing the coiled wire from the barrier, 7). applying a tension to the cinch string to configure the sheet material in a pouch configuration for encapsulating the morcellated tissue located on the top surface within the sheet material, and 8). removing the sheet material in the pouch configuration from the human body.

Furthermore, the described features and advantages of the disclosure may be combined in various manners and embodiments as one skilled in the relevant art will recognize. The disclosure can be practiced without one or more of the features and advantages described in a particular embodiment.

Further advantages of the present disclosure will become apparent from a consideration of the drawings and ensuing description.

BRIEF DESCRIPTION OF THE DRAWINGS

The advantages and features of the present disclosure will become better understood with reference to the following more detailed description and claims taken in conjunction with the accompanying drawings, in which like elements are identified with like symbols, and in which:

DESCRIPTIVE KEY

Figure 1:
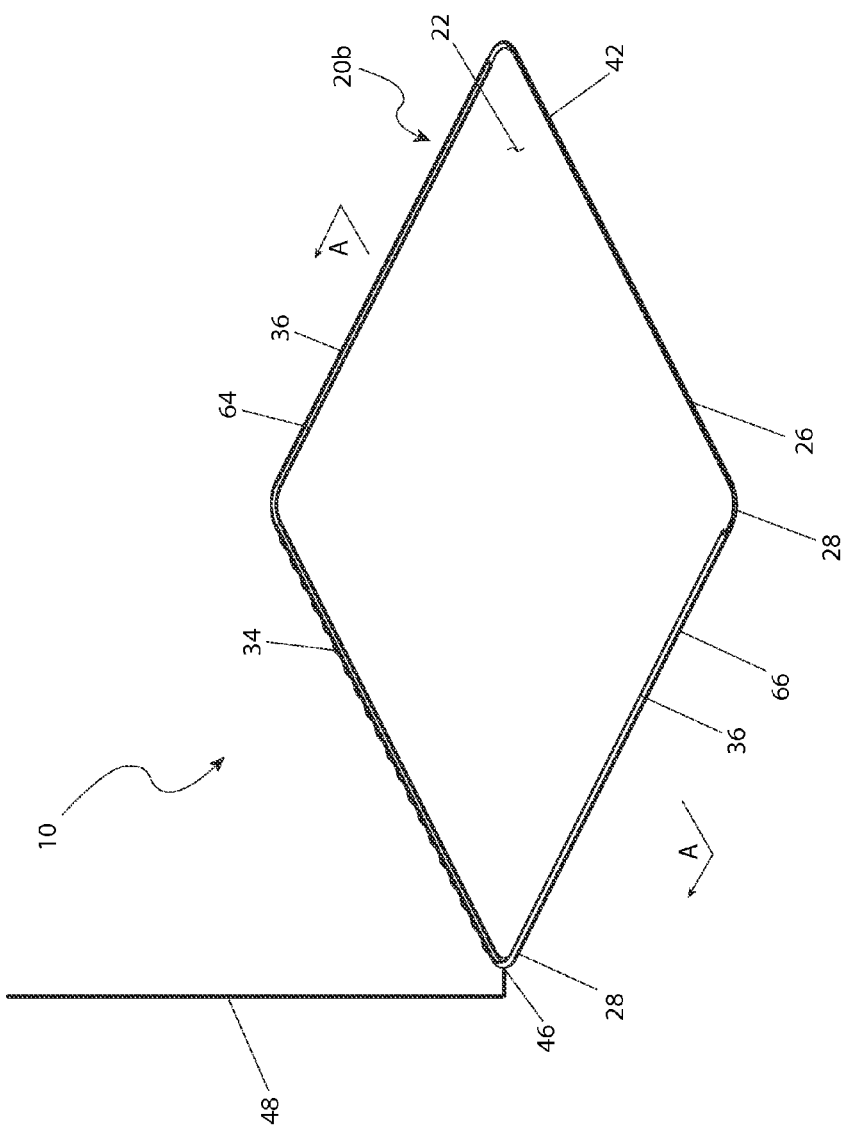
FIG. 1 is a perspective view of a morcellated tissue apparatus depicted being configured as a mat, in accordance with one embodiment of the present invention.

10 morcellated tissue apparatus
20a roll
20b mat
20c pouch
22 top
24 bottom
26 peripheral edge
28 corner
34 distal edge
36 lateral edge
42 hem
44 tunnel 46 aperture
48 cinch string
52 interior
54 exterior
62 wire
64 bather
66 barrier cover

DETAILED DESCRIPTION OF THE PREFERRED EMBODIMENT

In accordance with the invention, the best mode is presented in terms of a one or more of the disclosed embodiments, herein depicted within FIGS. 1 through 5. However, the disclosure is not limited to a single described embodiment and a person skilled in the art will appreciate that many other embodiments are possible without deviating from the basic concept of the disclosure and that any such work around will also fall under its scope.

Further, those skilled in the art will recognize that other styles and configurations can be incorporated into the teachings of the present disclosure, and that the example configurations shown and described herein are for the purpose of clarity and disclosure and not by way of limitation.

As used herein, the singular terms "a", "an", and "the" do not denote a limitation of quantity, but rather denote the presence of at least one (1), as well as a plurality of, the referenced items, unless the context clearly indicates otherwise.

As used herein, the terms "first", "second", "third", etc. are used as labels to describe various elements, features, and/or components, and are not intended to impose ordinal, positional, or hierarchical requirements on the referenced items, unless other indicated. For example, such terms may be used to distinguish one (1) element from another element.

As used herein, relative terms such as "front", "rear", "left", "right", "top", "bottom", "below", "above", "upper", "lower", "horizontal", or "vertical" are used to describe a relationship of one (1) element, feature and/or region to another element, feature and/or region as illustrated in the figures.

Referring to FIGS. 1-5, disclosing a morcellated tissue apparatus (herein referred to as the "apparatus") 10, where like reference numerals represent similar or like parts. The apparatus 10 provides a means to collect upon a mat 20b extraneous loose (e.g., morcellated) tissue resulting from the sectioning, cutting, or otherwise breaking up larger tissue specimens (e.g., organs) during a laparoscopic surgical procedure and to gather the mat 20b into a pouch 20c for extraction of the morcellated tissue.

Figure 2:
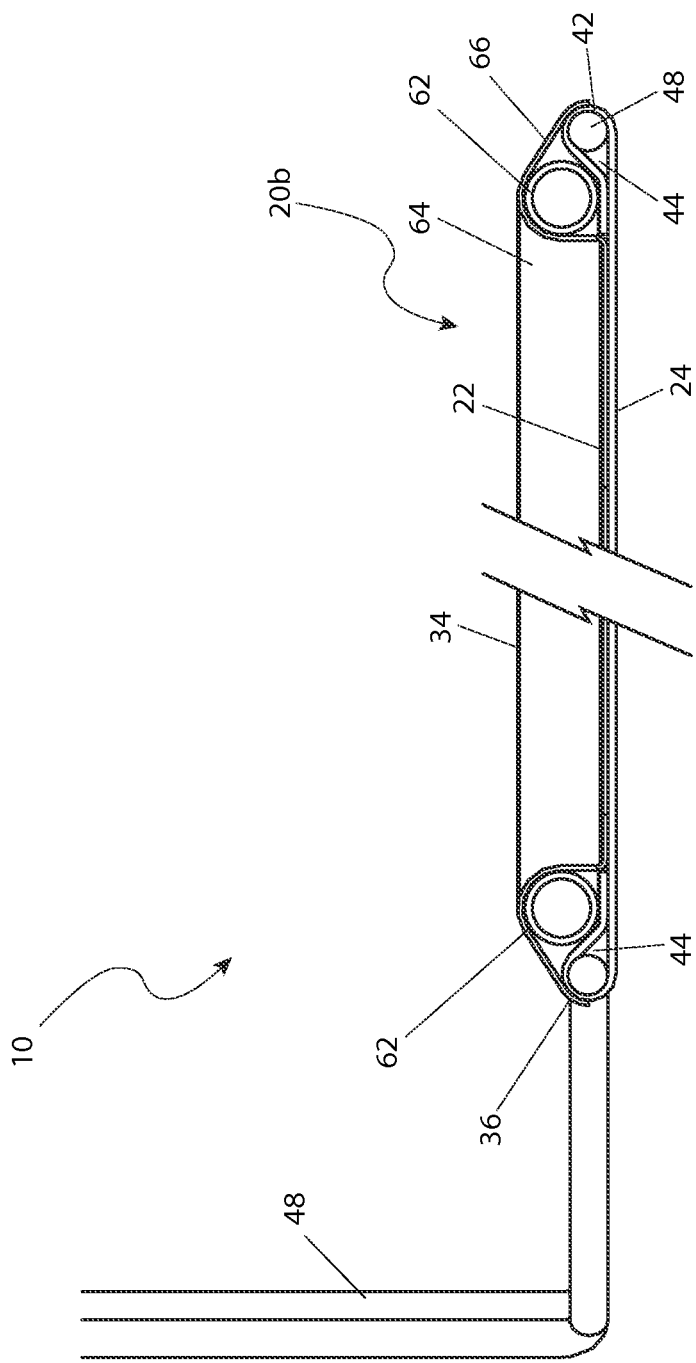
FIG. 2 is a section view along line A-A of FIG. 1 of the morcellated tissue apparatus.
Figure 5:
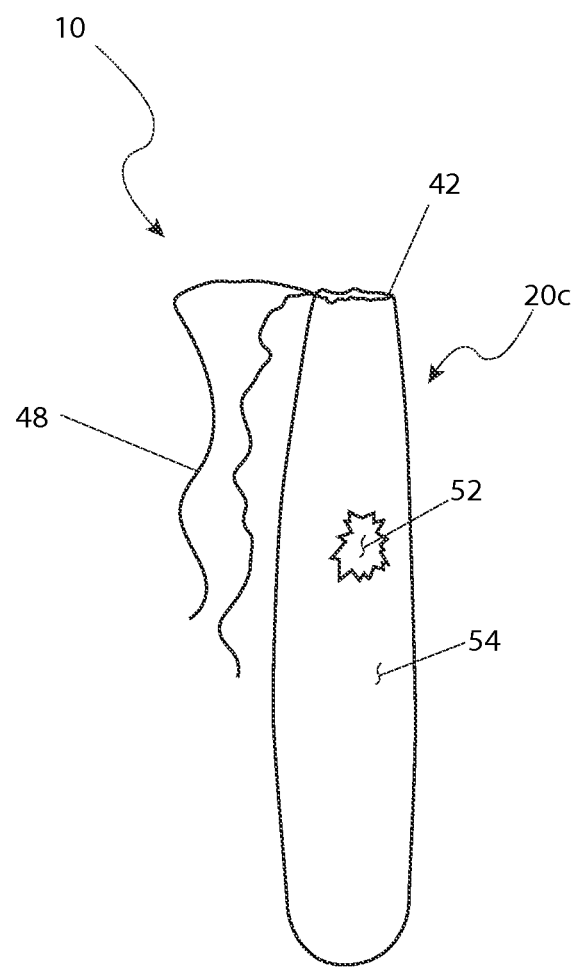

Referring now to FIGS. 1, 2, and 5, perspective views of the apparatus 10 configured as a mat 20b (e.g., in a layed-flat configuration), configured as a roll 20a, and configured as a pouch 20c, respectively, according to one (1) embodiment of the present invention, is disclosed. The apparatus 10 can be configured as a roll 20a (also referred to herein as a roll configuration 20a) to be inserted within a patient, as a substantially planar mat 20b (also referred to herein as a mat configuration 20b) to be arranged to cover a portion of a patient's bowel, and as a pouch 20c (also referred to herein as a pouch configuration 20c) containing tissue to be extracted from the patient.

The mat 20b, as seen in FIG. 1, has a top 22 along an upper surface to receive any tissue sloughed off during the morcellation procedure, and a bottom 24 (FIG. 2) along a lower surface and in contact with any subjacent organ(s). The mat 20b is preferably composed of a generally square sheet of a pliable thermoplastic material and as such may be presented in a variety of colors and opacity ranges. The mat 20b is provided with a hem 42 that is formed by folding a peripheral edge 26 of the mat 20b back upon itself and securing the peripheral edge 26 to the top 22, for example, with an ultrasonic seal.

Within the hem 42 is an encircling tunnel 44 for the disposition of a cinch string 48, as illustrated in FIG. 2. The cinch string 48 is preferably a thermoplastic monofilament configured to draw up the peripheral edges 26 of the mat 20b so as to form the pouch 20c, as seen in FIG. 5. The ends of the cinch string 48 enter and exit from the tunnel 44 through an aperture 46, preferably located at a corner 28 of the mat 20b. As one (1) example, the cinch string 48 may be of sufficient length to extend to the exterior of the abdominal cavity for eventual use.

Figure 4:
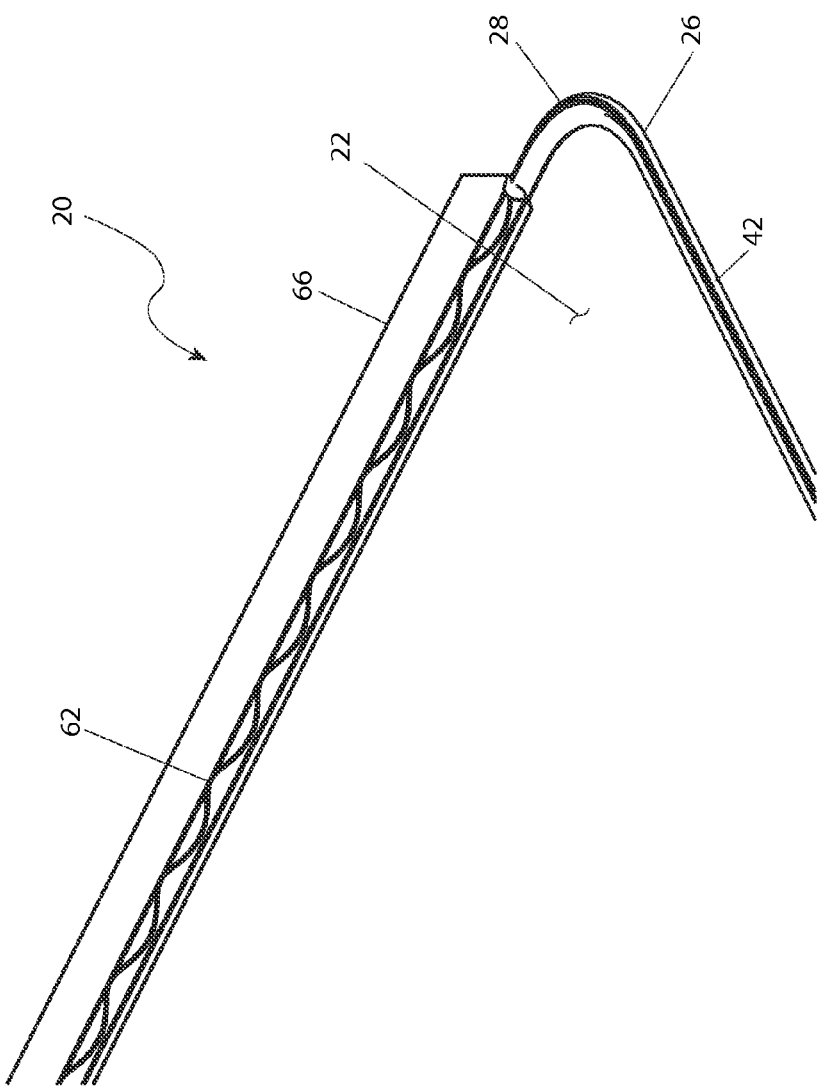
FIG. 4 is a cutaway view of a wire of the morcellated tissue apparatus in accordance with one embodiment of the present invention; and, FIG. 5 is a perspective view of the morcellated tissue apparatus depicted being configured as a pouch, in accordance with one embodiment of the present invention.

Disposed along a distal edge 34 and the two (2) lateral edges 36 of the mat 20b is a barrier 64 that is intended to prevent any tissue from rolling or sliding off of the mat 20b after having been deposited thereon. The bather 64 is configured to be a coil of wire 62 secured within a barrier cover 66 attached to the top 22 of the mat 20b, as depicted in FIG. 4. The coil diameter should be sufficient to present the desired obstacle to the departure of any tissue. The barrier cover 66 is preferably a layer of thermoplastic material similar to, or consistent with, the constituent material of the mat 20b.

Figure 3:
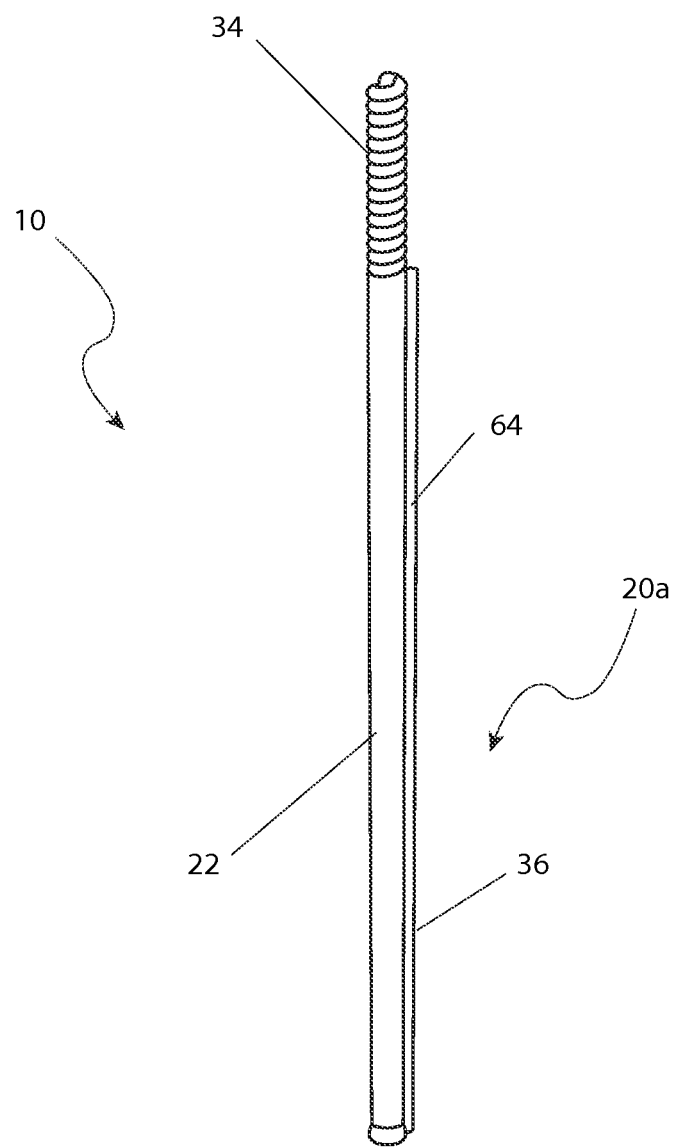
FIG. 3 is a perspective view of the morcellated tissue apparatus depicted being configured as a roll, in accordance with one embodiment of the present invention.

The advantage of coiling the wire 62 is to beneficially exploit the spring effect of the wire 62 in order allow the mat 20b to be extended from the roll 20a configuration illustrated in FIG. 3. The apparatus 10 is placed (e.g., configured) as the roll 20a having a rolled configured to be inserted through a fifteen millimeter (15 mm) cannula into the abdominal cavity in at least one (1) embodiment.

As seen in FIG. 4, the bather cover 66 can be sliced open with a scalpel to expose the wire 62 for extraction of the wire 62 prior to drawing (e.g., configuring) the mat 20b into a pouch 20c. The removal of the wire 62 will facilitate the eventual collapse of the mat 20b by removing the tendency of the wire 62 to spread the mat 20b.

Referring now to FIG. 5, a perspective view of the apparatus 10 configured as the pouch 20c for extraction according to one embodiment of the present invention, is disclosed. Subsequent to the complete removal of the wire 62 from the barrier cover 66, the cinch string 48 would be pulled to close the mat 20b into a pouch 20c. Additional manipulation of the apparatus 10 with forceps may be required to accomplish the successful completion of this procedure.

The aperture 46 of the tunnel 44 may need to be elevated and steadied while the cinch string 48 is pulled in order to secure items within the apparatus 10. The top 22 of the mat 20b will be drawn into the interior 52 of the pouch 20c while the bottom 24 will be reconfigured to be an exterior 54 surface. All of the material previously disposed upon the top 22 will now be secured within the interior 52 and the pouch 20c can be extracted through the cannula.

Those skilled in the art will recognize that other styles and configurations of the disclosed apparatus 10 can be easily incorporated into the teachings of the present disclosure, and only particular configurations have been shown and described for purposes of clarity and disclosure and not by way of limitation of scope.

One embodiment of the disclosed method for utilizing the apparatus 10 includes the following steps: 1). acquiring a model of the apparatus 10; 2). inserting the roll 20a through a cannula into an abdominal cavity at a proper time in the procedure; 3). allowing the roll 20a to open into the mat 20b; 4). positioning the mat 20b to protect the bowel and receive any tissue sloughed off from the morcellation procedure; 5). slicing open the barrier cover; 6). retracting the wire 62; 7). manipulating the mat 20b to properly close into the pouch 20c by pulling the ends of the cinch string 48; and 8). extracting the pouch 20c from the abdominal cavity. The extracted morcellated tissue may be analyzed for diagnosis or discarded as required.

The foregoing descriptions of specific embodiments have been presented for purposes of illustration and description. They are not intended to be exhaustive or to limit to the precise forms disclosed and many modifications and variations are possible in light of the above teachings. The embodiments were chosen and described in order to best explain principles and practical application to enable others skilled in the art to best utilize the various embodiments with various modifications as are suited to the particular use contemplated.

What is claimed is:

1. An apparatus for collection and removal of morcellated tissue, said device comprising:
    a flexible sheet material comprising a first surface, a second surface, and a perimeter edge; and
    a cinch string operably coupled to said perimeter edge,
    wherein said sheet material is sequentially configurable from a first configuration as a roll for insertion into a body, to a second configuration as a substantially planar mat, wherein said first surface defines a planar top surface of said mat and said second surface defines a planar bottom surface of said mat, for collection of said morcellated tissue, to a third configuration as a pouch, wherein said first surface defines an interior surface of said pouch and said second surface defines an exterior surface of said pouch, for removal of said morcellated tissue from said body,
    wherein said sheet material further comprises a barrier extending upwardly from said first surface and disposed along at least a portion of said perimeter edge, said barrier comprising a barrier cover connected to said first surface and a coiled wire disposed between said barrier cover and said first surface;
    wherein said coiled wire biases said sheet material in said second configuration as said mat; and
    wherein a tension force applied to said cinch string reconfigures said sheet material from said second configuration as said mat to said third configuration as said pouch.

2. The apparatus of claim 1, wherein said sheet material comprises a hem formed along said perimeter, and wherein said cinch string is disposed within said hem.

3. The apparatus of claim 2, wherein said hem defines an internal tunnel, wherein said tunnel comprises an aperture, and wherein said cinch string extends outwardly from said aperture.

4. The apparatus device of claim 1, wherein said sheet material comprises a pliable thermoplastic.

5. The apparatus of claim 1, wherein said cinch string comprises a thermoplastic monofilament.

6. The apparatus of claim 1, wherein said sheet material comprises a substantially square shape.

7. The apparatus of claim 6, wherein said sheet material comprises a hem formed along said perimeter, wherein said hem defines an internal tunnel, and wherein a cinch string is disposed within said tunnel.

8. The apparatus of claim 7, wherein said tunnel comprises an aperture, and wherein said cinch string extends outwardly from said aperture.

9. The apparatus of claim 8, wherein said aperture is located at a corner of said square shape of said sheet material.

10. An apparatus for collection and removal of morcellated tissue, said device comprising:
    a flexible sheet material comprising a rectangular shape, said sheet material further comprising:
        a first surface;
        a second surface opposite said first surface; and,
        a perimeter edge defining said rectangular shape;
    a cinch string operably coupled to said perimeter edge of said sheet material; and
    a coiled wire coupled to said perimeter edge of said sheet material,
    wherein said sheet material is sequentially configurable from a first configuration as a roll for insertion into a human body, to a second configuration as a substantially planar mat, wherein said first surface defines a planar top surface of said mat and said second surface defines a planar bottom surface of said mat, for collection of said morcellated tissue, to a third configuration as a pouch, wherein said first surface defines an interior surface of said pouch and said second surface defines an exterior surface of said pouch, for removal of said morcellated tissue from said human body,
    wherein said coiled wire biases said sheet material in said second configuration as said mat, and
    wherein a tension force applied to said cinch string reconfigures said sheet material from said first configuration as said mat to said second configuration as said pouch.

11. The apparatus of claim 10, wherein said sheet material further comprises a hem formed along said perimeter edge, said hem defining an internal tunnel, said tunnel comprising an aperture disposed at a corner of said sheet material;
    wherein said cinch string is disposed within said tunnel and extends outwardly from said aperture.

12. The apparatus of claim 11, wherein said sheet material further comprises a barrier extending upwardly from said first surface.

13. The apparatus of claim 12, wherein said barrier is disposed along at least a portion of said perimeter edge.

14. The apparatus of claim 13, wherein said barrier comprises a barrier cover connected to said first surface, wherein said coiled wire is disposed between said barrier cover and said first surface and wherein said coiled wire extends said barrier cover perpendicularly beyond said top surface of mat for retaining said morcellated tissue on said top surface of said mat when said sheet material is in said second configuration.

* * * * *